US007037867B2

(12) United States Patent
Yu et al.

(10) Patent No.: US 7,037,867 B2
(45) Date of Patent: May 2, 2006

(54) ARTIFICIAL BONE GRAFT SUBSTITUTE USING CALCIUM PHOSPHATE COMPOUNDS AND METHOD OF MANUFACTURING THE SAME

(75) Inventors: Hyun Seung Yu, Seoul (KR); Kug Sun Hong, Seoul (KR); Choon Ki Lee, Seoul (KR); Dong Ho Lee, Seoul (KR); Sang Lim Lee, Seoul (KR); Bong Soon Chang, Seoul (KR); Su Jin Kim, Seoul (KR); Chang Kyun Lim, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 459 days.

(21) Appl. No.: 10/273,265

(22) Filed: Oct. 18, 2002

(65) Prior Publication Data
US 2003/0193106 A1 Oct. 16, 2003

(30) Foreign Application Priority Data
Apr. 10, 2002 (KR) .................. 10-2002-0019520

(51) Int. Cl.
*C04B 35/447* (2006.01)
*B28B 1/00* (2006.01)
*A61F 2/28* (2006.01)
(52) U.S. Cl. .................. 501/1; 623/23.56; 623/23.61; 623/16.11
(58) Field of Classification Search .................. 501/1; 623/23.56, 23.61
See application file for complete search history.

(56) References Cited

U.S. PATENT DOCUMENTS

| 6,323,146 B1 * | 11/2001 | Pugh et al. ..................... 501/1 |
| 6,585,946 B1 * | 7/2003 | Bonfield et al. ............. 423/308 |
| 6,846,493 B1 * | 1/2005 | Pugh et al. .................. 424/423 |
| 2004/0078087 A1 * | 4/2004 | Kim et al. ................ 623/23.56 |
| 2005/0049715 A1 * | 3/2005 | Ito et al. ..................... 623/23.5 |

FOREIGN PATENT DOCUMENTS

| JP | 07-291723 | * 11/1995 |
| KR | 2002096521 | * 12/2002 |

OTHER PUBLICATIONS

C.K. Lee, et al., "Comparison of Osteosynthesis According to Compositions of Porous Calcium Phosphate Graft", International Society for Ceramics in Medicine, Bioceramics, vol. 14.
45th Fall Congress of the Korean Orthopaedic Association, Oct. 18-20, 2001, Hilton Hotel, Seoul, Korea.
Journal of Korean Society of Spine Surgery, vol. 8, No. 4, Dec. 2001.

* cited by examiner

*Primary Examiner*—Karl Group
(74) *Attorney, Agent, or Firm*—Rosenberg, Klein & Lee

(57) ABSTRACT

A bone graft substitute using magnesium substituted calcium phosphate compounds and a method of manufacturing the same is provided in which the bone graft substitute is used for recovering bones damaged due to a bone fracture. The method of manufacturing a bone graft substitute includes the steps of mixing powdered calcium pyrophosphate and a magnesium included compound to thereby obtain a composition, pressure-forming the compositions to obtain a plastic body; and sintering the plastic body.

6 Claims, 8 Drawing Sheets

ARTIFICIAL BONE GRAFT SUBSTITUTE USING CALCIUM PHOSPHATE COMPOUNDS AND METHOD OF MANUFACTURING THE SAME

BACKGROUND OF THE INVENTION

1. Field of the Invention

The present invention relates to a bone graft substitute and a method of manufacturing the same, and more particularly, to a bone graft substitute using calcium phosphate compounds and a method of manufacturing the same, in which the bone graft substitute is used for recovering bone defects damaged due to a bone fracture using calcium phosphate compounds.

2. Description of the Related Art

In general, a classical and general bone graft is an autograft. The autograft has advantages of good osteogenic capacity and having no risks of infection of infective diseases or immune response. However, it is difficult to obtain a sufficient amount of bones from patient, and inflammation may occur in a donor site. Thus, an allograft or xenograft is not satisfactory due to difficulties of obtaining bones to be grafted through a bone bank, or problems of a delay in a bony union together with risks of infection of infective diseases and immune response.

In order to solve the above-described problems, a recent research and development of bone graft substitute of osteogenic capacity similar to autograft has been being extensively performed.

Calcium phosphate compounds get into the spotlight as candidates for bone replacement. Hydroxyapatite (HA, $Ca_{10}(PO_4)_6(OH)_2$) is a principal inorganic component occupying a bone mass of 60–70%. The HA is superior in view of biocompatibility and has good osteoconductive property. Thus, studies of developing the HA ceramics into bone graft substitutes and applying the same clinically have been being vividly proceeded.

However, since the HA ceramics have a very low solubility in a living body, it remains in the body for a long time. As a result, a complete replacement of new bone is hindered.

There are a number of calcium phosphate compounds which can be used as a bone graft substitute. A representative one among them is tricalcium phosphate (TCP; $Ca_3(PO_4)_2$), or calcium pyrophosphate (CPP; $Ca_2P_2O_7$) in addition to the HA.

A variety of calcium phosphate compounds vary in dissolution rate in a living body, respectively. It is known that the extent of dissolution decreases in the following order: CPP>TCP>>HA. A material of rapid dissolution in the body is called a biodegradable material, which includes TCP and CPP.

An ideal biodegradable material should keep strength and durability during slow degradation to accomplish a complete substitution into a new bone. Also, it has an dissolution rate which is possibly identical to a bone growth rate. However, any materials which meet all the above-described conditions has not been found yet.

By the way, optimal compounds or compositions which may be consistent with the above-described conditions can be determined by adjusting a composition of calcium phosphate compounds whose solubilities in a living body differ from each other appropriately.

SUMMARY OF THE INVENTION

To solve the above problems, it is an object of the present invention to provide an bone graft substitute and a method of manufacturing the same, using calcium phosphate compounds having a good osteoconductive property and proper biodegradation rate.

To accomplish the above object, there is provided a bone graft substitute using calcium phosphate compounds characterized in that any one selected from the group consisting of magnesium oxide (MgO), magnesium substituted calcium pyrophosphate ($Ca_{2-x}Mg_xP_2O_7$), magnesium pyrophosphate ($Mg_2P_2O_7$), and calcium magnesium pyrophosphate ($CaMgP_2O_7$), and each powder of calcium pyrophosphate ($Ca_2P_2O_7$) or calcium pyrophosphate including tricalcium phosphate ($Ca_3(PO_4)_2$) of 10 weight-ratio percent [wt %] or less, are mixed and pressure-formed and then sintered at a temperature of 1000~1300° C.

According to another aspect of the present invention, there is also provided a method of manufacturing an artificial bone substitute, comprising the steps of: mixing each powder of calcium pyrophosphate ($Ca_2P_2O_7$) or calcium pyrophosphate including tricalcium phosphate ($Ca_3(PO_4)_2$) of 10 weight percent [wt %] or less, and a magnesium included compound, to thereby obtain a composition; pressurizing the composition or forming a porous body, to thereby obtain a green body; and sintering the green body.

The magnesium included compound is any one selected from the group consisting of magnesium oxide (MgO), magnesium substituted calcium pyrophosphate ($Ca_{2-x}Mg_xP_2O_7$), magnesium pyrophosphate ($Mg_2P_2O_7$), and calcium magnesium pyrophosphate ($CaMgP_2O_7$).

The magnesium oxide (MgO) is mixed at 0.1~10 wt % in the composition, the magnesium substituted calcium pyrophosphate ($Ca_{2-x}Mg_xP_2O_7$) is mixed at 0.1~75 atom % in the composition, and magnesium pyrophosphate ($Mg_2P_2O_7$) and calcium magnesium pyrophosphate ($CaMgP_2O_7$) are mixed at 0.2~75 wt % in the composition, respectively.

In the sintering step, a sintering temperature is in the range of 1000~1200° C. In the case that the sintering temperature is lower than 1000° C., a relative density of sintered body is lower than 90%, which causes strength and durability to be lowered. In the case that the sintering temperature is higher than 1200° C., the sintered material is melted or broken due to a crack caused by volume change from a phase transition.

As described above, the bone graft substitute manufactured by the present invention is advantageous over the existing bone graft substitute in view of a bony union, a bone bonding strength, and a biodegradation property.

BRIEF DESCRIPTION OF THE DRAWINGS

The above object and other advantages of the present invention will become more apparent by describing the preferred embodiments thereof in more detail with reference to the accompanying drawings in which.

PREFERRED EMBODIMENTS OF THE INVENTION

A preferred embodiment of the present invention will be described below with reference to the accompanying drawings.

An bone graft substitute using calcium phosphate compounds and a method of manufacturing the same according to the present invention provides a bioceramic composition in which magnesium added β-calcium pyrophosphate, or calcium pyrophosphate and tricalcium phosphate are mixed.

The magnesium is added in the form of magnesium oxide (MgO) or in the form of a compound ($Ca_{2-x}Mg_xP_2O_7$) in which part of calcium is substituted with magnesium, where the magnesium oxide is preferably added by 0.1~10 wt % in the composition, and the magnesium substituted compound is preferably added by 0.1~75 atom % in the composition.

The added magnesium enhances elaborateness of calcium pyrophosphate mixed calcium pyrophosphate and tricalcium phosphate ($Ca_3(PO_4)_2$) of 10 weight percent [wt %] or less, and lowers the sintering temperature by 100° C. Also, the magnesium is one of elements included in the human bones where the composition manufactured by the present invention will be used, and occupies 0.5 wt % or so within the human bones. Thus, the added magnesium does not only enhance sintering of the calcium pyrophosphate, but also improve bioaffinity if the composition has elements more similar to the human bones.

As described above, the present invention has used magnesium oxide (MgO), magnesium substituted calcium pyrophosphate ($CaMgP_2O_7$), or magnesium pyrophosphate ($Mg_2P_2O_7$), as a sintering material, in order to enhance sintering of β-calcium pyrophosphate or calcium pyrophosphate mixed with a small amount of tricalcium phosphate. Hereinbelow, a content of each sintering material will be described.

First, it is preferable that magnesium oxide (MgO) is included in calcium pyrophosphate by 0.1~10 wt %. If a content of MgO is less than 0.1 wt %, MgO does not influence upon sintering. However, if a content of MgO is not less than 10 wt %, MgO disappears completely since positive ions are too excessive and thus only the tricalcium phosphate ($Ca_3(PO_4)_2$) is left.

Calcium pyrophosphate ($CaMgP_2O_7$) or magnesium pyrophosphate ($Mg_2P_2O_7$) can be added rather than addition of the magnesium oxide (MgO), in order to expect the same effects. In this case, it is preferable that calcium pyrophosphate ($CaMgP_2O_7$), or magnesium pyrophosphate ($Mg_2P_2O_7$) is added within the range of 0.2~75 wt %. If calcium is substituted with magnesium at 0.2 wt % or less, the magnesium substitution does not influence upon sintering. If calcium is substituted with magnesium at 75 wt % or more, an excessive liquid phase is formed. Accordingly, ceramic grains grow abnormally to thereby produce closed pores within the grains and prevent sintering rather. The added magnesium reacts with calcium pyrophosphate or tricalcium phosphate to thereby form a liquid phase. This liquid phase rearranges the ceramic grains and activates chemical diffusion between grains to improve sintering property and mechanical strength.

Hereinbelow, the present invention will be described in more detail through various embodiments. However, the scope of the present invention is not limited to the following embodiments.

First through Third Embodiments, and First Comparative Example

Magnesium oxide (MgO), calcium magnesium pyrophosphate ($CaMgP_2O_7$), and magnesium pyrophosphate ($Mg_2P_2O_7$) have been added in calcium pyrophosphate of 99.9% quantitatively as illustrated in the following Table 1, respectively, and mixed in a zirconia ($ZrO_2$) ball mill for 24 hours and then dried rapidly. Thereafter, the mixture is ground in a pestle and pressure-formed under a isostatic pressure of 1000 kg/cm², to thus obtain pellets of about 8 mm in diameter and about 3 mm in thickness.

A specimen of a first comparative example where the additive has not been added and specimens of first through third embodiments where the additive has been added have been sintered at 1000~1150° C. for 2 hours. Here, a heating rate was 5° C./min, and thereafter furnace-cooled. A phase analysis and a bulk density measurement of the sintered specimens were performed and the results have been shown in the following Table 1.

(1) Phase Analysis

The powder compacts have been sintered and then observed by an X-ray diffraction method in order to identify phase.

(2) Bulk Density

The bulk density of each of the sintered specimens have been measured by the Archimedes' method. A relative density was calculated from the measured density and theoretical density.

TABLE 1

| Kind of additive | Amount of additive | Kind of phase | Possible sintering temperature | Maximum relative density |
|---|---|---|---|---|
| 1st comparative example | X | X | β-CPP | 1150° C. | 93% |
| 1st embodiment | MgO (wt %) | 0.2 | β-CPP, β-TCP | 1150° C. | 93% |
| | | 0.5 | β-CPP, CMPP, β-TCP | 1150° C. | 95% |
| | | 1 | β-CPP, CMPP, β-TCP | 1150° C. | 99% |
| | | 3 | β-CPP, CMPP, β-TCP | 1100° C. | 96% |
| | | 5 | β-TCP, CMPP, β-CPP | 1100° C. | 96% |
| | | 10 | β-TCP, CMPP | 1050° C. | 97% |
| | | 12 | β-TCP | 1300° C. | 99% |
| 2nd embodiment | $Mg_2P_2O_7$ (wt %) | 0.2 | β-CPP | 1150° C. | 93% |
| | | 0.5 | β-CPP, CMPP | 1150° C. | 95% |
| | | 5 | β-CPP, CMPP | 1150° C. | 98% |
| | | 10 | β-CPP, CMPP | 1100° C. | 99% |
| | | 20 | β-CPP, CMPP | 1050° C. | 98% |
| | | 50 | MPP, CMPP | 1050° C. | 97% |
| | | 70 | MPP, CMPP | 1150° C. | 95% |
| | | 75 | MPP, CMPP | 1150° C. | 92% |

TABLE 1-continued

|  | Kind of additive | Amount of additive | Kind of phase | Possible sintering temperature | Maximum relative density |
|---|---|---|---|---|---|
| 3rd embodiment | CaMgP$_2$O$_7$ | 1 | β-CPP, CMPP | 1150° C. | 92% |
|  |  | 3 | β-CPP, CMPP | 1150° C. | 98% |
|  |  | 5 | β-CPP, CMPP | 1100° C. | 99% |
|  |  | 10 | β-CPP, CMPP | 1050° C. | 97% |
|  |  | 50 | CMPP, β-CPP | 1050° C. | 97% |
|  |  | 70 | CMPP | 1050° C. | 95% |
|  |  | 75 | CMPP | 1000° C. | 93% |

※ CPP: Calcium pyrophosphate (Ca$_2$P$_2$O$_7$), CMPP: Calcium magnesium pyrophosphate (CaMgP$_2$O$_7$), MPP: Magnesium pyrophosphate (Mg$_2$P$_2$O$_7$), TCP: Tricalciumphosphate (Ca$_3$(PO$_4$)$_2$)

As illustrated in Table 1, the maximum sintered relative density of the calcium pyrophosphate in the first comparative example is 93%. Thus, a sintering property need to be enhanced in order to be manufactured into an artificial bone requiring a high mechanical strength. As illustrated in the first through third embodiments, the sintered density of each of the specimens where magnesium oxide, calcium magnesium pyrophosphate, or magnesium pyrophosphate has been added at an appropriate ratio was increased in comparison with that of the specimen of the calcium pyrophosphate where the addictive has not been added. In the case of some specimens, it was possible to sinter the specimens with a high density even at a temperature of 1050° C. lower than those of the other specimens by 100° C. The reason why the sintering was enhanced resides in the fact that the calcium magnesium pyrophosphate whose melting point is 1120° C. and secondary phase magnesium substituted pyrophosphate (Ca$_{2-x}$Mg$_x$P$_2$O$_7$, 0<x<1) whose melting point is lower than 1120° C. coexist in the specimens where the additive has been added. The specimens added with the additive become a liquid phase between 1000° C. and 1150° C., to thus rearrange the particles of the calcium pyrophosphate to resultantly enhance sintering. If a bulk density increases, a mechanical strength is enhanced, which has been illustrated in the following Table 2.

TABLE 2

|  |  | Compression strength (MPa) |
|---|---|---|
| 1st comparative example | Calcium pyrophosphate | 519.5 ± 40.6 |
| 3rd embodiment | Calciumpyrophosphate + 10 wt % calcium magnesium pyrophosphate | 782.3 ± 2.5 |

As illustrated in Table 2, the compression strength in the third embodiment was larger by about 1.5 times than that of the first comparative example where the additive has not been added. Thus, it is expected that a mechanical strength will be increased together with an increase in a bulk density as illustrated in the third embodiment.

Meanwhile, in order to identify an osteoconduction property of a bone graft substitute manufactured from the compositions produced according to the first through third embodiments, an experiment where the bone graft substitute has been compared with an autogeneous bone grafting product and existing artificial bone grafting products will be described below.

In order to compare the bone graft substitute according to the present invention with the other bone grafting substitutes including the autograft, the grafting materials have been grouped into 9 groups as illustrated in the following Table 3, and compared with one another.

TABLE 3

|  | Grafting materials |
|---|---|
| 1st Group | Positive control (autograft) |
| 2nd Group | Negative control (non-graft) |
| 3rd Group | Devitalized Bovine Bone (Lubboc ®) |
| 4th Group | Calcium Sulfate Pellet (CSP) |
| 5th Group | HA |
| 6th Group | HA 50% + TCP 50% |
| 7th Group | TCP |
| 8th Group | TCP 50% + calcium pyrophosphate 50% |
| 9th Group | Calcium pyrophosphate |

1. Manufacturing of Porous Calcium Pyrophosphate Grafting Substitutes

In order to prepare various types of porous calcium phosphate graft substitutes for comparable experiments, each grafting substitute has been made through the following methods, respectively.

γ,β-Ca$_2$P$_2$O$_7$ (99.0%, Junsei, Japan) and CaCO$_3$ (99.8%, High Purity Chemistry, Japan) have been prepared quantitatively so that a Ca/P ratio became 1.67, and then mixed and calcinated. Then, hydroxyapatite (HA) has been synthesized and ground, sprayed and dried to thereby obtain a powder of the hydroxyapatite (HA).

3γ,β-Ca$_2$P$_2$O$_7$+4CaCO$_3$→Ca$_{10}$(PO$_4$)$_6$(OH)$_2$+4CO$_2$↑

Likewise, γ,β-Ca$_2$P$_2$O$_7$ and CaCO$_3$ have been prepared quantitatively so that a Ca/P ratio became 1.5, and then mixed, calcinated, ball-milled and dried. Then, a powder of β-TCP has been made.

γ,β-Ca$_2$P$_2$O$_7$+CaCO$_3$→Ca$_3$(PO$_4$)$_2$+CO$_2$↑

γ,β-Ca$_2$P$_2$O$_7$ which has been in the powder form of the raw material has been calcinated, ground and dried to thereby obtain a powder of β-CPP.

The hydroxyapatite (HA) and the β-TCP calcinated powder have been mixed and ground at a 1:1 ratio, to thereby obtain a HA/β-TCP composition powder. In this manner, a β-TCP/β-Ca$_2$P$_2$O$_7$ composition powder has been made. The magnesium oxide (MgO) of 1 wt % has been added in each powder.

Each of the powders manufactured as described above has been coated on a polymeric sponge. A porous body has been formed and then sintered to remove a polymeric sponge. Accordingly, various types of porous graft substitutes have been completed.

A polyurethane sponge has been used as a polymeric sponge which becomes a frame of the porous bone graft substitute, in which pores are all connected by interconnected pores three-dimensionally without clogging, in which the polyurethane sponge has a size of a pore of about 500 μm, and a size of an interconnected pore of about 300 μm.

By using the polyurethane sponge, a porous bone graft substitute having the same structure as those of the pores and interconnected pores formed in the polyurethane sponge, can be manufactured.

That is, the pores and the interconnected pores formed in the porous bone graft substitute are determined according to the structure of the polyurethane sponge which is used as a raw material. The pores and the interconnected pores, particularly, the interconnected pores are very important elements for a growth of a new bone.

An interconnected pore differs in concept from a commonly said pore. The interconnected pore is defined as a size of a diameter in a cross-sectional area where a pore and another pore are connected with each other.

The porous bone graft substitute according to the present invention is grafted into a bone defects A new bone grows up through the pores in the bone graft substitute, to finally achieve a complete bony union. Here, in order to accomplish a complete bony union, pores located nearby should be completely connected by interconnected pores. Since the interconnected pores provide spaces where blood vessels for supplying nutrition for bone cells are formed, sizes of the interconnected pores should keep the sizes of about 200~600 µm so that blood vessels can be formed naturally.

If a size of an interconnected pore is 200 µm or less, it is inappropriate to form blood vessels for supplying nutrition for bone cells into the interconnected pore. If a size of an interconnected pore is 600 µm or more, there are too many empty spaces. As a result, it takes much time to fill the pores with a new bone.

Figure 3:
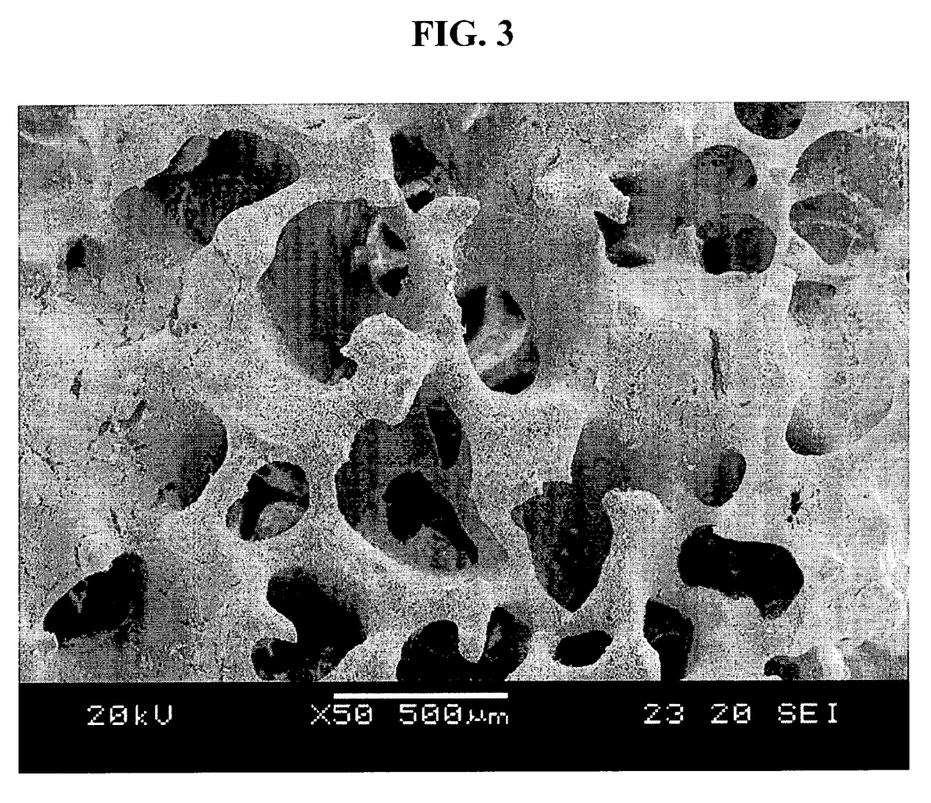
FIG. 3 is a photograph showing a microstructure of a bone graft substitute manufactured by a polymeric sponge method.

The thus-manufactured porous bone grafting substitute has a pore ratio of 75% as shown in FIG. 3, and the sizes of the pores and the interconnected pores do not differ greatly from the polyurethane sponge used as the interconnected pore raw material.

2. Implantation

1) Grafting Objects and Experimental Groups

Experimental animals have been male New White rabbits weighing 3~3.5 kg from New Zealand. Total ninety New White rabbits have been divided into nine groups, that is, ten rabbits have been assigned into one group. In nine groups, a negative control group where only a cortical bone in a horizontal protrusion has been removed and no graft has been performed and a positive control group where an autogeneous bone graft has been performed, have been included. In order to be compared with artificial bone products which are being used clinically in Korea, control groups have been also established, in which a devitalized bovine bone (Lubboc®) being a heterogeneous bone product and a commercialized calcium sulfate pellet (CSP) have been grafted. These four kinds of control groups and the five groups grafted with the calcium phosphate compounds of five kinds of compositions manufactured as described above, that is, a porous HA, a TCP, a calcium pyrophosphate, a HA/TCP complex and a TCP/calcium pyrophosphate complex, have been established as illustrated in Table 3.

2) Grafting Surgery

Ketamine and Xylazine have been intramuscularly injected by 150 mg and 30 mg, respectively, to thereby put a respective specimen under general anesthesia. Then, an aseptic surgery has been performed. A vertical incision has been operated along a polar protrusion around the post articulation in the fifth and sixth lumbar vertebrae on both sides, and the horizontal protrusion in the fifth and sixth lumbar vertebrae on both sides has been exposed by the paraspinal approach through respectively different incisions. Then, a rear cortical bone of the exposed horizontal protrusions has been removed with a cutting tool such as a burr of 4.0 mm in diameter, and bone fragments have been washed. Thereafter, a grafting substitute of about 2.5 cc has been connected with the horizontal protrusion at either side, to thereby complete the grafting surgery. Immediately after surgical operation, Terramycine has been intramuscularly injected and then the specimen animals have been freely made active in a breeding farm. In the case of the autogeneous bone grafting group, a separate muscular membrane incision has been operated on the rear-upper hipbone poles on both sides through an identical skin incision, and then autogeneous bones have been gathered from the hipbone to be used as grafting materials. In the case of the non-graft group, only a rear cortical bone has been removed and then no grafting substitutes have been inserted.

3) Gathering Specimens

All animals of all the groups were killed by the air embolization method at the 12th weeks after surgery, and all the fifth and sixth lumbar vertebrae and the fusion masses on both sides have been gathered carefully so that they have not been broken.

3. Evaluation

1) Radiographical Examination

At the 2nd, 4th, 6th and 8th weeks after the surgical operation, and immediately before being killed at the 12th week, a simple radiographical examination has been performed in the rear-front lumbar vertebrae, and then fusion of the grafting substitutes, creation of new bones and a degree of bony union have been observed. In particular, it has been observed whether a boundary shading of each grafting substitute block whose shading had been obvious immediately after the surgical operation has become obscure in comparison with the peripheral portions, whether a radiographical penetration shading between the respective blocks whose shading had been obvious before the surgical operation has become similar to the penetration shading of the peripheral blocks, and whether the fusion masses connecting between the adjacent horizontal protrusions have been created. Then, the appearance and time at which each view and opinion has resulted have been compared with one another.

2) Blood Test

At the 2nd, 4th, 6th, 8th and 10th weeks after the surgical operation, and immediately before being killed at the 12th week, blood of about 2 cc has been gathered from the ear vein of each New White rabbit, and then concentration of calcium and phosphate in the serum have been measured. Then, it has been observed how concentrations of the calcium and phosphate in the serum have been changed according to solution of the grafting substitutes. A numerical value of each term after surgical operation has been compared with the numerical value measured before the surgical operation, through a paired t-test. By doing so, a significancy of the change has been evaluated.

3) Macrography and Manual Palpation

In all experimental examples, the fifth and sixth lumbar vertebrae including the fusion masses between the horizontal protrusions on both sides immediately after being killed haven been gathered carefully so that an unnecessary external force has not been applied if possible. The front and rear vertical ligaments, the ligament between the polar protrusions, the yellow ligament, the rear articulation membrane, and the inter-spinal plate have been completely cut off so that no connection structures exist between the spinal bodies except for the fusion masses. Then, the creation and appearance of the fusion masses and the change of the grafting substitutes have been observed with the naked eyes. A bending force has been applied with both hands so that the fusion masses have not been broken. Then, the solidity and fusion extent of the fusion masses have been evaluated. It has been judged as a fusion in the case that a bending strength and an elasticity similar to those of a bone tissue have been possessed while a continuity has been being kept.

Meanwhile, it has been judged as a non-fusion in the case that two spinal bodies have been already separated during preparation of specimens since a fusion structure between the horizontal protrusions have not been formed, and the fusion masses have shown a bending strength and elasticity similar to those of the edge tissues. An examination with an optical microscope has been performed with respect to two samples per each group among the specimens which has got through the manual palpation and a biomechanical examination has been performed for the other samples.

4) Biomechanical Examination

A screw of 3 mm in diameter has been inserted in the front and rear direction so that the screw has passed through the center of the top and bottom spinal bodies in the direction of the thalamus plane. Then, the spinal bodies has been made located at the center of the screw. A fixing tool has been connected to a steel chain so that tensile force has worked uniformly in the front and rear portions if possible, to thereby prevent a rotational stress from being applied. By connecting this steel chain to Instron (Instron 8500, Instron corporation, USA), a tension test has been performed in the vertical direction of the fusion mass. A load (N) at the time when a resistance has been sharply reduced has been determined as a break point.

5) Examination with an Optical Microscope

In order to perform a non-calcination optical microscope examination, a sample fixed immediately after being killed has been embedded with methyl methacrylate after dehydration. Using a diamond saw, the sample has been cut traversely inparallel with the fusion mass, so that the fusion mass and the horizontal protrusion have been included, and then dyed with H&E (Hematoxylin and Eosin), to thereby fabricate a slide. Under the optical microscope, the fusion mass has been discriminated into the grafting substitute, the new bone, and the edge tissue by each part in the fusion mass, to thereby read out a growth of the bone.

In order to perform a calcination optical microscope examination, a sample specimen fixed immediately after being killed and another sample specimen having got through the biomechanical examination have been fixed in a formalin solution and then soaked into 5% nitric acid solution for four days to perform calcination. After calcination, the specimen embedded into the paraffin has been cut off with 4 μm in thickness in the vertical direction in parallel with the fusion mass so that the fusion mass and the horizontal protrusion have been included. Likewise, the specimen has been dyed with H&E, and then the appearance and degree in the creation of the new bone have been examined under an optical microscope.

4. Results

Ten rabbits among the total ninety New White rabbits were died during breeding after surgical operation. Five rabbits were excluded since an infection due to the surgical operational injury has been found. Thus, a total loss ratio of the experimental specimens was about 17%, and thus the above-described evaluation results have been analyzed based on the remaining 75 rabbits.

1) Radiographical Examination

A bone fusion report has not been observed in a non-grafting group (negative control group). In contrast, in the case of the autogeneous bone grafting group (positive control group), a boundary portion of a grafting block has started to be obscured from the 4th week after surgical operation, a radiographical penetration shading between the grafting blocks has started to increase from the 4th week after the surgical operation, and a bone fusion mass shading having shown a relatively uniform bone density has been formed at the 12th week. However, at the portion where the cortical layer bone has been mixed during grafting, the cortical layer bone shading has remained until the 12th week even though the strength has got lowered gradually. In the case of the Lubboc® grafting group, the radiographical non-penetration of the grafting substitutes has been too lower than that of the autogeneous bone on the whole. Thus, the boundary of the grafting substitutes blocks have been already obscure from the 2nd week after surgical operation, and the radiographical penetration vacancy shading between the blocks has been increased from the 4th week. A fusion mass shading of a relatively uniform density has been shown from the 6th week after surgical operation, and then still maintained till the 12th week. In the case of the CSP grafting group, a grafting substitute pellets have been solved sharply from the 2nd week after surgical operation, an extremely small number of the pellets has remained at the 4th week, the pellets have been absorbed completely from the 6th week, the pellets have been completely absorbed at the 6th week, and thus the fusion mass shading has not been formed. In the case of the porous HA grafting group, a boundary of the blocks has been obscure at the 6th week, the vacancy shading between the grafting substitute blocks has been increased, and the block structure has been almost maintained for the 12 weeks, without any deformation. In the case of all of the porous HA/TCP grafting group, TCP/calcium pyrophosphate grafting group, and the calcium pyrophosphate grafting group, the boundary portions between the grafting blocks have been obscure at the 4th week after surgical operation, the vacancy between the blocks has disappeared at the 6th week, and the fusion mass shading has completed at the 12th week but the radiographical non-penetration has still remained at the particle center. Thus, it has been shown that part of the block structure has been maintained at the central portion particularly. In the case of the TCP grafting group, the boundary portion of the grafting substitutes has been obscure from the 2nd week after surgical operation, differently from the other calcium phosphate grafting substitutes, the vacancy between the grafting substitute particles has disappeared from the 4th week after surgical operation, and the block structure has started to lose from the 8th week, and finally the relatively uniform fusion mass shading has shown at the 12th week.

2) Calcium and Phosphate in the Serum

Figure 1A:
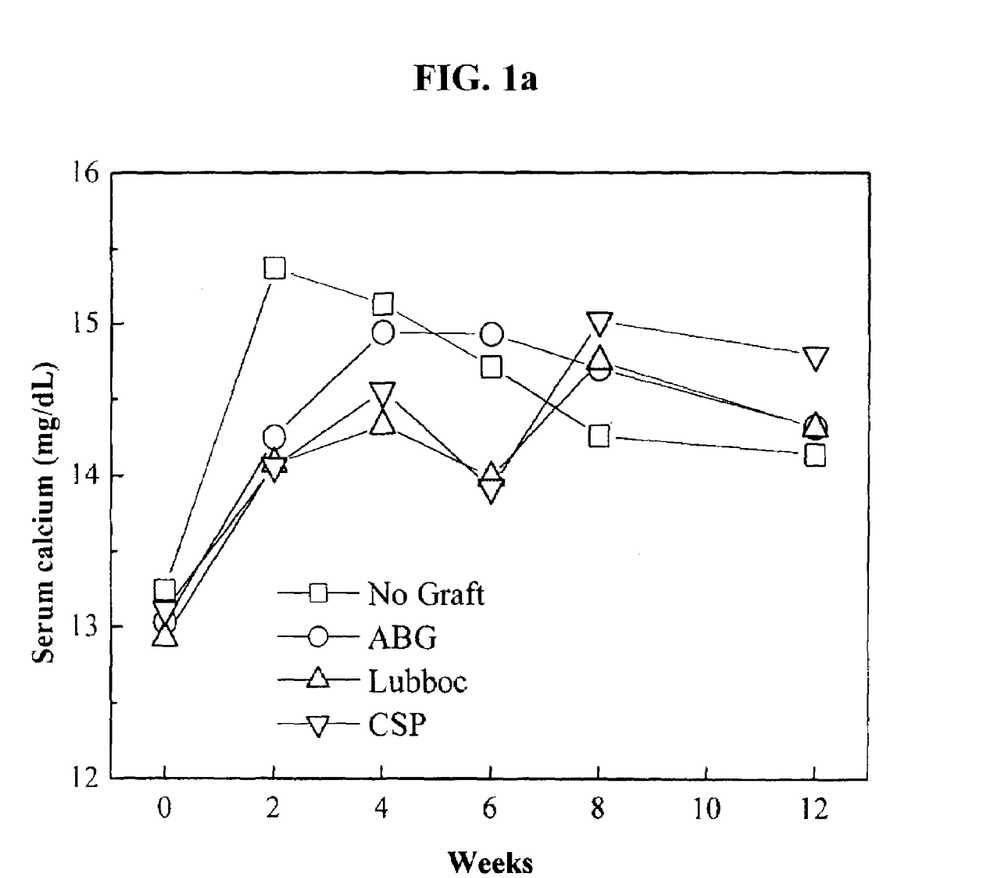
FIGS. 1A through 1D are graphical views for explaining a variation in calcium and phosphorus concentration with time in a blood serum after implantation in order to explain the present invention.
Figure 1B:
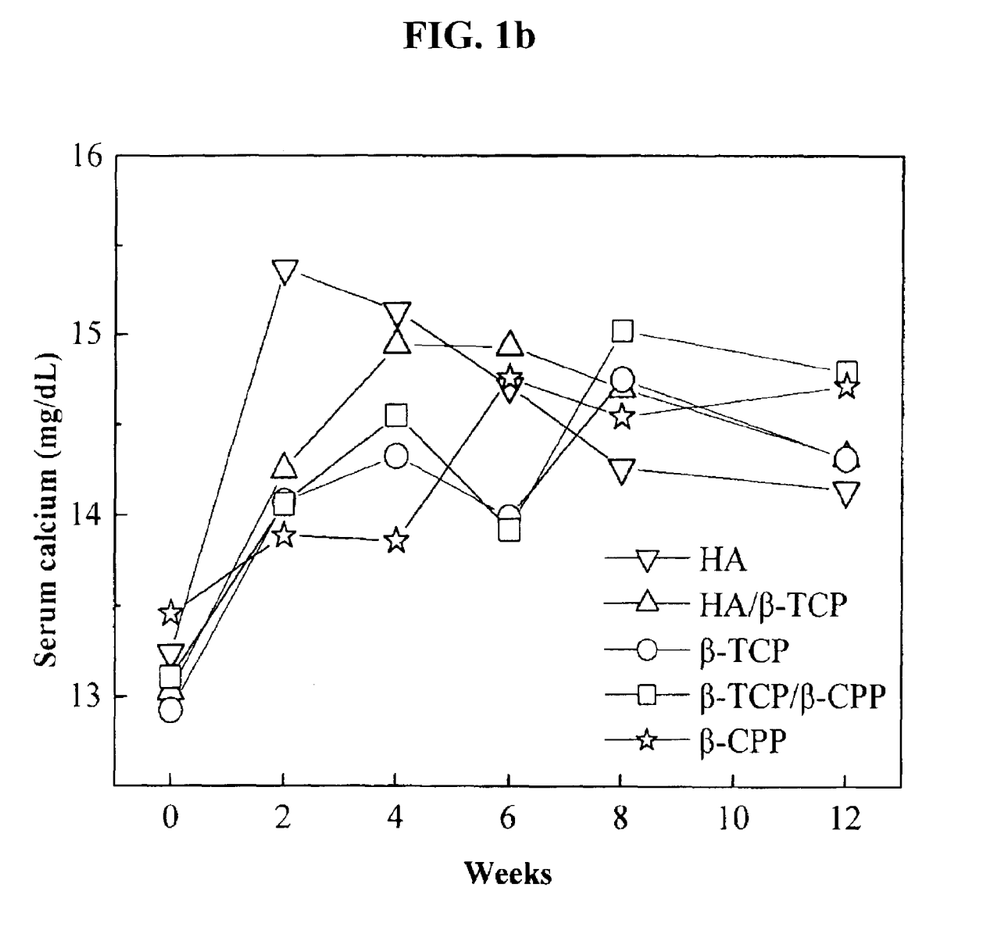

The calcium in the serum before surgical operation had no great difference between the specimens, and had also no significant differences between the groups. By analyzing all the specimens before surgical operation, a reliability section of 95% significance level has been determined. The range was 11.7~14.6 mg/dL which was regarded as a normal value of the calcium in the blood plasma of the New White rabbit. In the case of the non-graft group, the calcium value was increased significantly from the 4th through 12th weeks, in comparison with that obtained before surgical operation. According to the increasing trend, a plateau period was formed after the 4th week and showed a stable appearance. Also, the average values from the 6th to 12th weeks were increased in excess of the normal calcium value. In the case of the autograft group, the calcium value was increased from the 2nd week to the 6th week after surgical operation, and formed a plateau period. The average values from the 6th to 12th weeks were increased in excess of the normal calcium value. In the case of the Lubbock® and CSP grafting groups and all calcium phosphate porous substitute grafting groups, the calcium values were also increased from the 2nd to 12th weeks similarly. The increasing trend was not progressive but a plateau period was formed once the calcium value had been increased. The increment had no great difference in comparison with the control group as shown in FIGS. 1A and 1B.

Figure 1C:
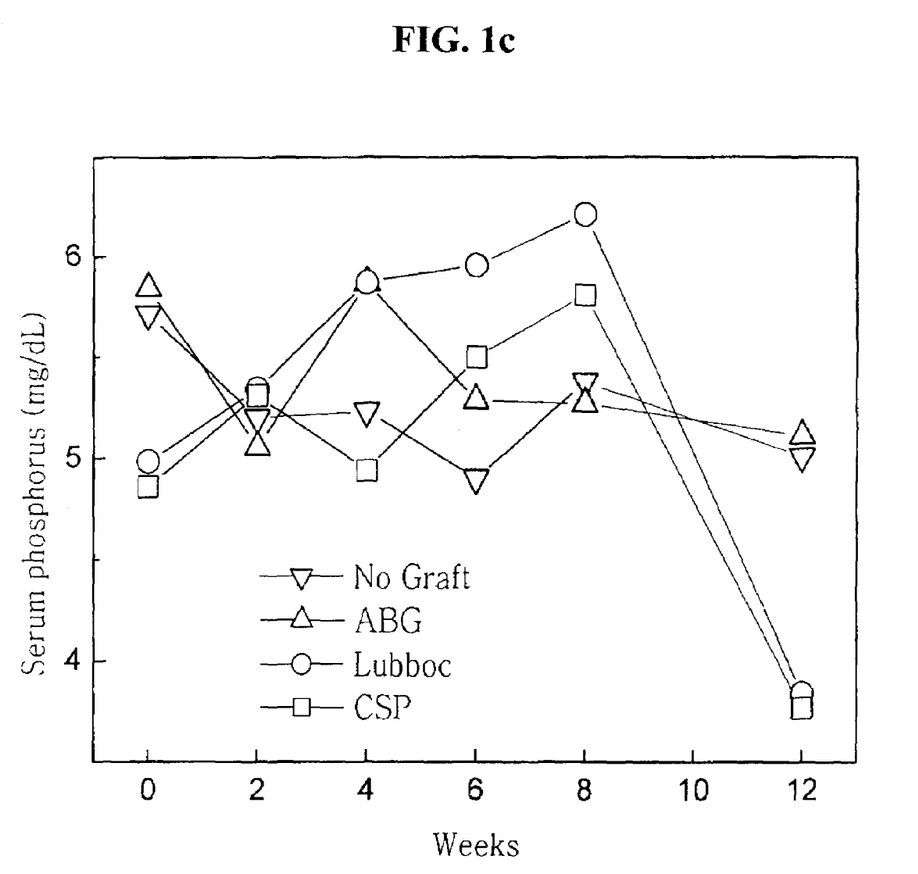
Figure 1D:
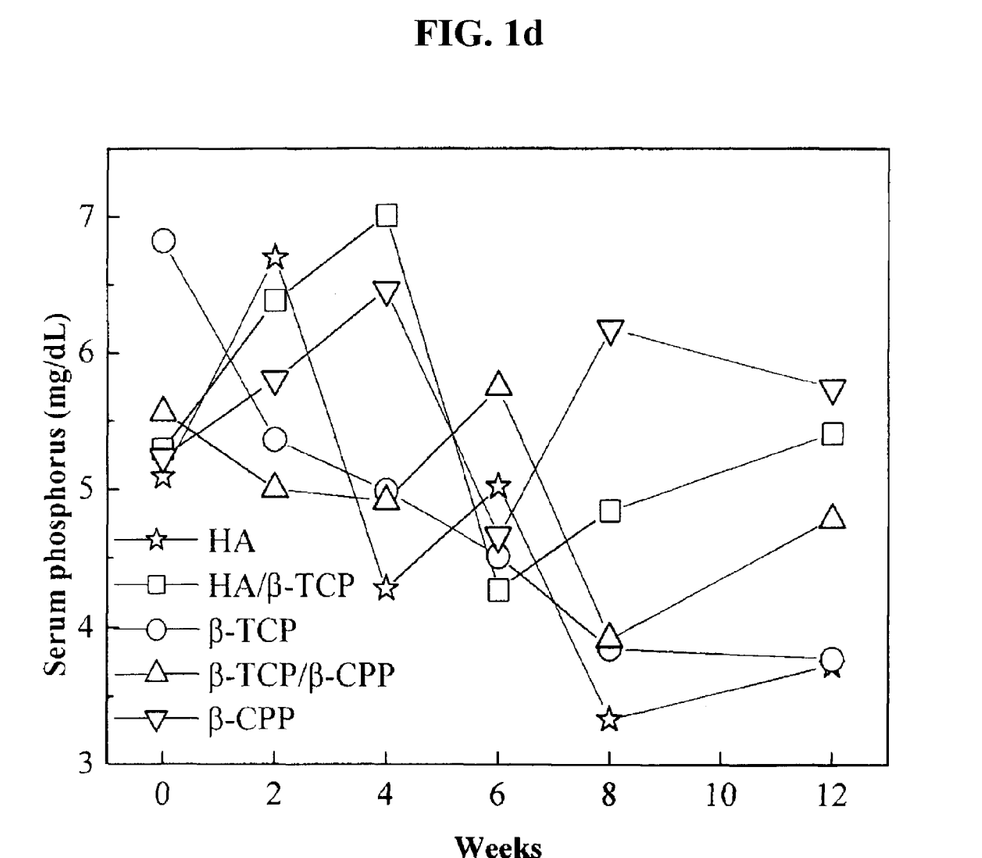

The phosphate in the serum before surgical operation had a severe variation between the specimens in comparison with the calcium, and had a great variation according to a time. Thus, it was difficult to observe a comparatively constant variation trend as in the calcium in the serum. By analyzing all the specimens before surgical operation, a reliability section of 95% significance level has been determined. The range was 3.1~7.8 mg/dL which was regarded as a normal value of the phosphate in the blood plasma of the New White rabbit. In the case of the non-graft group, the phosphate value was decreased somewhat all over the weeks, in comparison with that obtained before surgical operation. The statistically significant decrement was shown at the 2nd and 6th weeks after surgical operation. In the case of the autograft group, the phosphate value showed a significant decrement only at the 2nd week, and did not show a significant variation from the 4th week in comparison with that obtained before surgical operation. In the case of the other groups, an irregular variation was observed although the variation had a little difference. The numerical value had no great difference in comparison with the normal value and that of the control group as shown in FIGS. 1C and 1D.

3) Macrography and Manual Palpation

In the case of the autograft group and the porous CPP grafting group, solid bone fusion was observed in all the samples among the seven specimens. In the case of Lubboc® grafting group, solid bone fusion was in the six samples among the seven specimens. In the case of the porous HA grafting group, solid bone fusion was in the eight samples among the ten specimens. In the case of the porous HA/TCP grafting group, solid bone fusion was in the six samples among the ten specimens. In the case of the porous TCP/calcium pyrophosphate grafting group, solid bone fusion was in the five samples among the ten specimens. However, in the case of the porous TCP grafting group, bone fusion was only in the three samples among the eight specimens. Also, bone fusion was not in all the samples among the ten specimens in the case of the CSP grafting group, and among the nine specimens in the case of the non-grafting group. Thus, two spinal bodies were already separated during preparation of the specimens (refer to Table 4). In the statistical analysis through the Fisher's exact test, fusion ratios of the autograft group and the porous calcium pyrophosphate grafting group were significantly higher than those of the non-grafting group, CSP, TCP/CPP compositions and TCP grafting groups (P<0.05). Also, it was evaluated that fusion ratios of the Lubboc® and HA grafting groups were significantly higher than those of the non-grafting group and the CSP grafting group (P<0.05), and were superior to those of the TCP/calcium pyrophosphate composition and TCP grafting groups. However, a statistical significance was not found. In the macrography, a considerable number of portions of the porous structure were collapsed in all the samples in the case of the TCP grafting group, and part thereof was found as a powdered appearance. In the case of the TCP/calcium pyrophosphate, HA/TCP composition grafting groups, part of the porous structure was also found collapsed although there was a little difference.

4) Biomechanical Examination

In the case of the non-grafting group and the CSP grafting group, fusion masses connecting between the two horizontal protrusions of the spines were not formed in all the samples as described above. As a result, since two spinal bodies were separated during preparation of the specimens, it was not possible to perform a tensile strength test. Accordingly, a tensile load was set zero at the moment of breakage. The average tensile strengths of the porous HA and CPP grafting groups were highest in similarity with each other. In the statistical analysis through the nonparametric method by the Kruskall-Wallis test, these groups showed the significantly higher tensile strengths in comparison with the non-grafting group, Lubboc® and CSP grafting groups, TCP/calcium pyrophosphate and TCP grafting groups. The average tensile strengths of the autograft group and the porous HA/TCP grafting group were located in the middle of the values of the other groups, but had no significant differences in comparison with the other groups (refer to Table 4).

5) Examination with Optical Microscope

In the non-grafting group, a new bone was partly formed at the portion where a cortical layer bone had been removed, and a defective portion of the horizontal protrusion was regenerated. However, a bone growth in the gap between the horizontal protrusions was not observed.

Figure 2A:
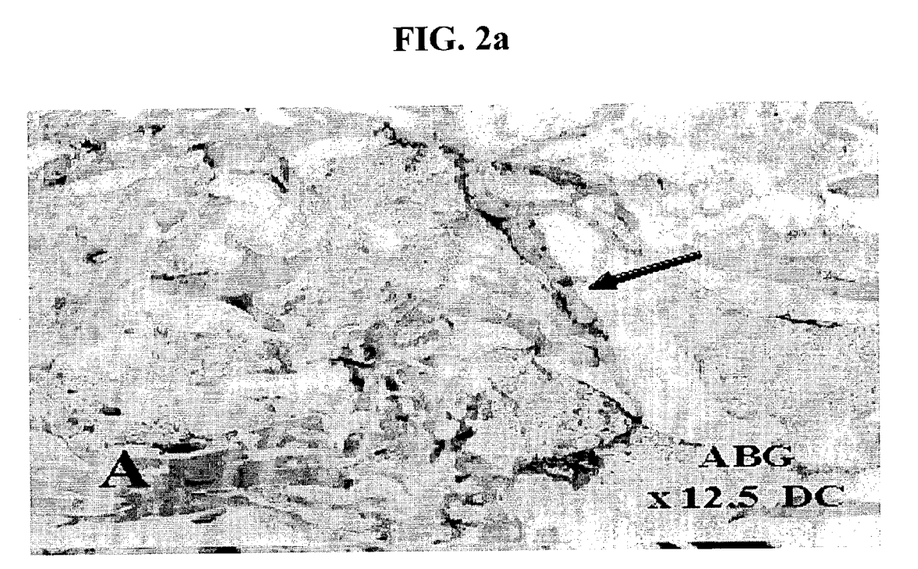
FIGS. 2A through 2F are histological photographs of each specimen in order to explain the present invention.

In the case of the autograft group, a plurality of osteoclasts were found in the periphery of the bone marrow column of the grafted bone and a new bone was vividly formed between the bone marrow column which was absorbed by the osteoclasts. Also, enchondral ossification was found in part. The maturity of the new bone was the most excellent and there were some places where the marrow was already completed in the inside of the new bone. However, in the case that the cortical layer bone of the grafted bone was placed perpendicular to the direction of the fusion mass and a bone absorption was not completed, the continuity of the fusion mass was interrupted as being the case (refer to FIG. 2A).

Figure 2B:
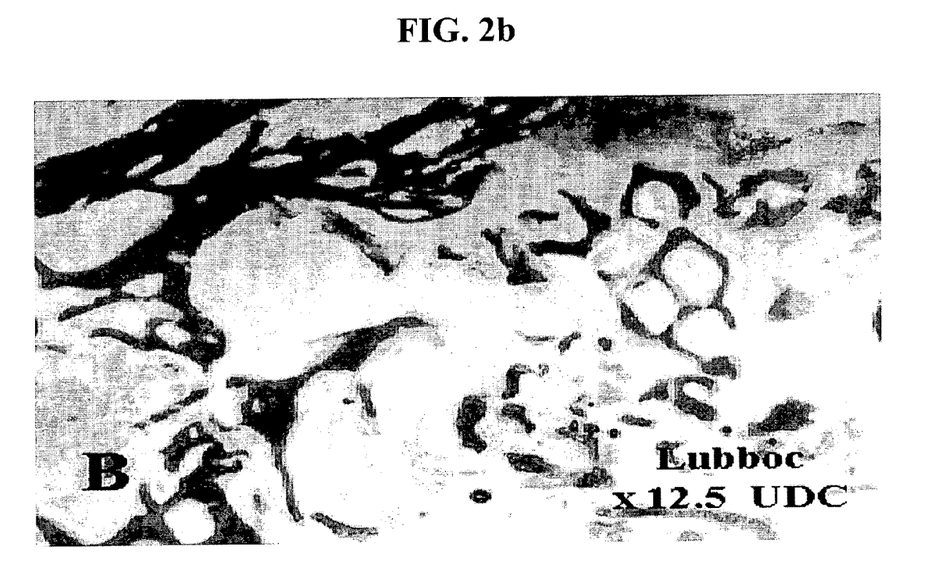

In the case of the Lubbock® grafting group, a considerable portion of the grafted substitutes was absorbed. As a result, a porous structure was lost, and a new bone was penetrated in the periphery of a necrotic bone. However, it was observed that textile tissues grew up in the periphery of the considerable portion of the necrotic bone, to thereby disturb a connectivity between bones. In particular, the central portion of the block was filled with most of the textile tissues (refer to FIG. 2B).

Figure 2C:
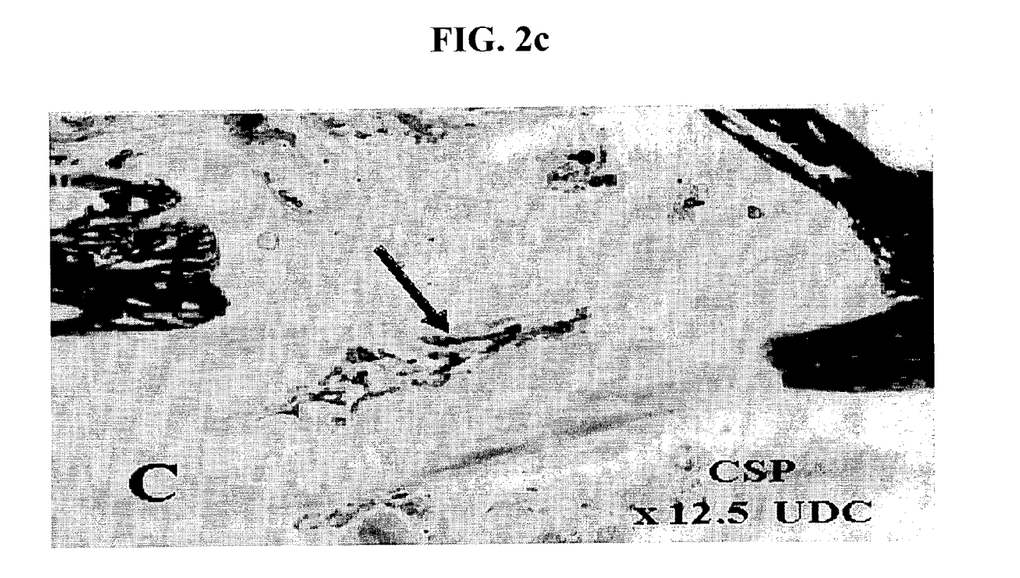

In the case of the CSP grafting group, the grafted substitute remainders which were remaining in a small quantity between the horizontal protrusions were observed and textile tissues occupied the vacancy almost without forming a new bone. In one sample, an independent new bone island was peculiarly observed between the grafted substitute remainders, but the degree was extremely insignificant. As a result, the independent new bone island did not contribute the formation of the fusion mass (refer to FIG. 2C).

Figure 2D:
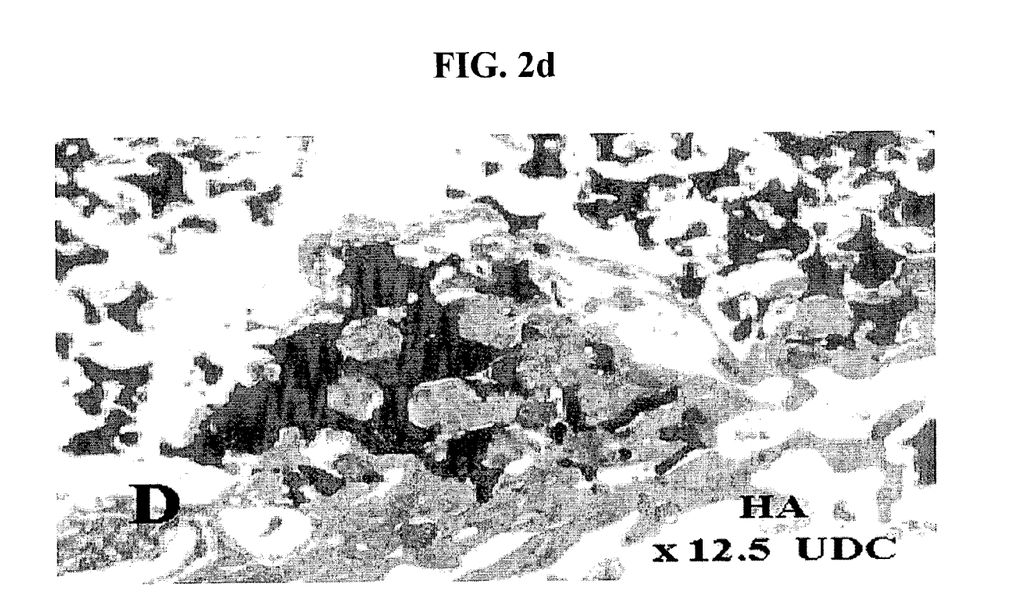

In the case of the porous HA grafting group, the structure and volume of the grafted substitutes were maintained in comparison with the other porous calcium phosphate grafting groups, which suggested a low solubility in the living body. A bone growth into the pores was much abundant in the periphery of the block, but the activity was lowered approaching in the central portion. This was a report which could be observed in common in all the porous calcium phosphate grafted substitutes (refer to FIG. 2D).

Figure 2E:
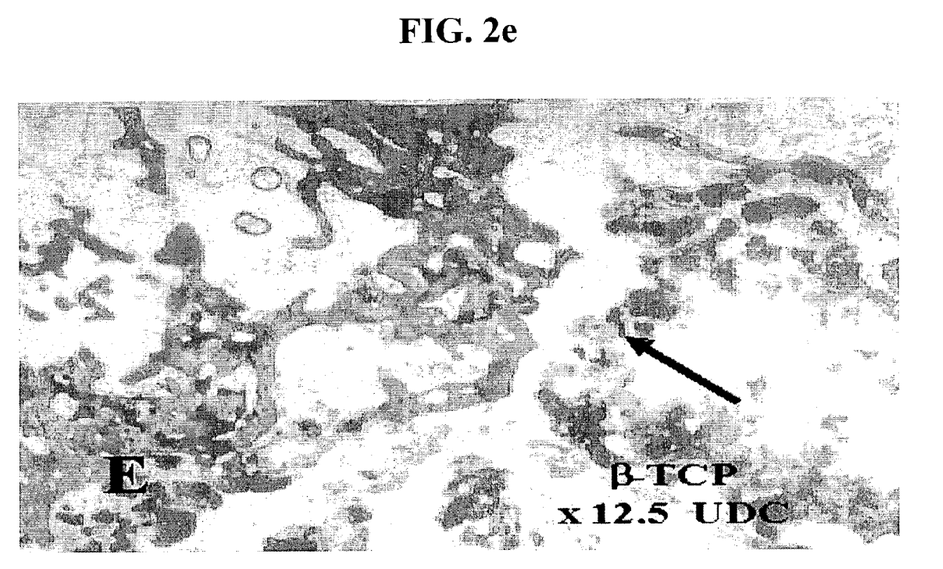
Figure 2F:
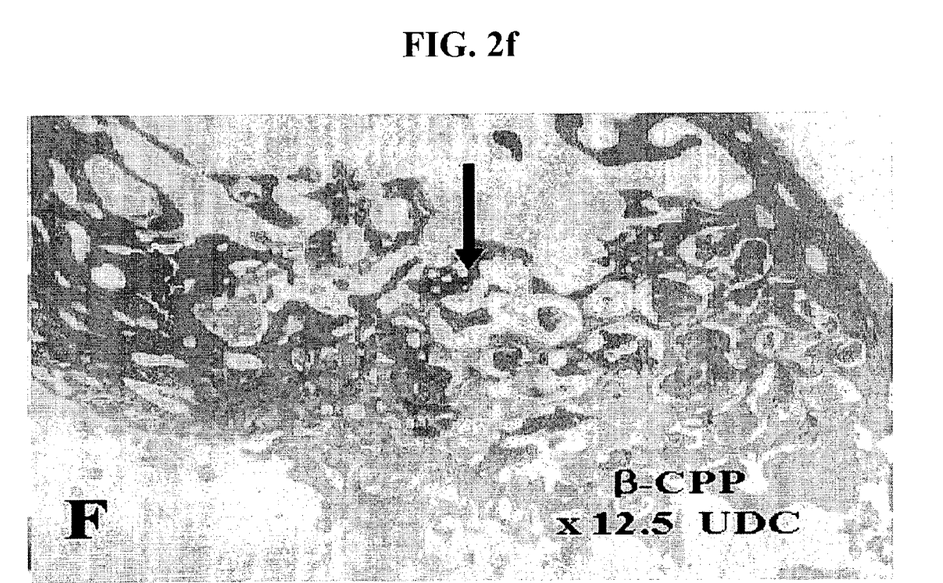

In the case of the CPP grafting group, the size of the pore was increased and the thickness of the wall between the pores was thin in comparison with the HA grafting group, which reflected a higher absorption. Meanwhile, the porous structure was well maintained and a new bone was abundantly formed into the porous structure. Also, a new bone showed an appearance of a mature bone whose lamellation was well accomplished (refer to FIG. 2F).

In the case of the HA/TCP, TCP, and TCP/CPP grafting groups, it was reported that the porous structure of the grafted substitutes was collapsed peculiarly, in which the degree was severe in order of TCP>TCP/CPP>HA/TCP. While the porous structure was collapsed, the pore size was decreased or the pore was disappeared. As a result, the grafted substitute became powdered. As the pore size was smaller, the new bone was not well formed, and stopped to be formed in the powdered portion. This report was typical in particular in the case of the TCP grafting group, in which a considerable number of particles were detached and scattered in the periphery of the scaffolds of the grafted substitute by which the pores were screened to thereby stop creation of the new bone, and part of textile tissues grew up into the small gaps between the particles to accordingly interrupt a continuity of the fusion mass (refer to FIG. 2E).

Typically, HA is classified into a stoichiometric HA and a nonstoichiometrc HA, in which the stoichiometric HA is $Ca_{10}(PO_4)_6(OH)_2$ whose calcium/phosphate ratio is accurately 1.67, and the nonstoichiometric HA chiefly means a Ca deficiency HA which is $\gamma Ca_{10}\text{-}x(HPO_4)x(PO_4)_6\text{-}x(OH)_2\text{-}x$ whose calcium/phosphate ratio is about 1.58 to 1.66. The nonstoichiometrc HA is superior relatively in a bone fusion speed, but unstable thermally. Thus, the nonstoichiometrc HA is decomposed into TCP (tricalcium phosphate; $Ca_3(PO_4)_2$) during sintering at a high temperature, which causes a mechanical strength to be lowered. As a result, the stoichiometric HA has been chiefly studied as a substitute for a grafted bone. However, the stoichiometric HA which has been manufactured by high pressure forming and high temperature sintering has too a low solubility in a living body. Accordingly, the stoichiometric HA is not nearly absorbed and remains, which prevents a bone lost portion from being substituted by the host bone. Considering the above point, a variety of multi-phase composites have been studied in which the composites maintain the durability until the new bone grows up and are decomposed gradually, to finally be substituted by the bone. However, the results of the studies on the bioaffinity according to the change in the composition of the porous calcium phosphate compounds have not been reported clearly.

Thus, in the present invention, a porous grafting substitute using a single or complex body of calcium phosphate compounds having various types of compositions whose decompositions in a living body are known to be different is manufactured, and grafted into a living body. Then, a bone creation and decomposition are observed and compared with that of the control group and the already-commercialized artificial bones. Through the results, the present invention provides a composition for expediting a bone creation and simultaneously being decomposed at an appropriate speed and substituted into a new bone completely.

In the present invention, a simple radiographical report has not reflected an actual fusion accurately. In the case of the TCP grafting group, all the samples showed a faster fusion mass formation report in comparison with those of the autograft group and the other calcium phosphate porous grafting groups. Also, in the present invention, since the density of the formed fusion mass has a uniform density all over the regions, it has been estimated that a solid and mature bone fusion would be accomplished. However, under the macrography and the microscopic examination, a porous structure of the grafted substitute has been collapsed and the size of the pore has been reduced and lost. A part of the pores has been ground in the form of a particle. The new bone creation continues until the collapse of the pores starts and stops if the collapse starts. Also, under the manual palpation examination, a solid none fusion was not been accomplished in the five samples among the eight specimens, and showed reportedly that the samples were connected by the textile tissues. Since the ground particles were uniformly distributed over the grafted portion, it was misunderstood as if a fusion mass of a uniform density had been formed under the simple radiographical examination. Such an error in the reading of the radiographical examination can be observed identically in the case of the HA/TCP grafting group and TCP/calcium phosphate grafting group where a collapse of the porous structure has been revealed, although there has been a difference in the degrees. In the case of the HA/TCP, $\beta$-TCP, and TCP/calcium phosphate grafting groups under the optical microscopic examination, a report on the porous structure collapse and the new bone proceeding stop due to the collapse have been observed peculiarly. The degrees were severe in order of TCP>TCP/calcium pyrophosphate>HA/TCP. From this point of view, it was presumed that the structure collapse was due to the TCP. It cannot be accurately found whether such a porous structure collapse is caused by being exposed to the circumstances in a living body to thereby reduce a mechanical strength, by a quick absorption in a living body, or by a complex function of the above-described two factors, which requires for an additional study.

In the case of the autograft group being a positive control group, a comparative uniform density has been found at the 12th week, and a shading of a bone fusion mass was formed, while revealing that the grafted substitute was completely connected with the horizontal protrusions of the top and bottom lumbar vertebrae. The hipbone of the New White rabbit differs from that of the human. In the case of the hipbone of the New White rabbit, the sponge bone is not abundant and a large amount of cortical layer bone is unevitably mixed during gathering of the autogeneous bone. These cortical layer bones have shown up on bone hardening lines at various portions of the grafted substitutes immediately after the grafting surgical operation. These bone hardening lines have been weakened gradually in their intensities but remained until immediately before being killed. If such a cortical layer bone part is located perpendicular to a fusion mass formation direction, the cortical layer bone part can function as an obstacle by which a continuous new bone growth is interrupted. As in the optical microscopic examination report, it has been estimated that a continuous bone osteoconduction has impeded, to thereby weaken a resistance force of the part in comparison with the other parts during a tensile strength test.

In the case of the Lubbock® grafting group, the radiographical non-penetration of the grafted substitute is very lower than that of the autogeneous bone. Accordingly, the boundary between the grafted substitutes has been obscure around from the 2nd week after surgical operation, and a shading of the fusion mass of a relatively uniform density has been revealed at the 6th week after surgical operation. Lubboc® is chiefly comprised of HA of the calf bone and collagen. In this case, since HA, that is, a content of calcium is relatively low, a boundary portion under the radiographical examination is not clear in comparison with the calcium phosphate porous body. For this reason, it can be misunderstood as if a fusion would be early achieved. Under the simple radiographical examination, it has been readout that an excellent bone fusion has been performed even in one sample where the bone fusion has not been performed among the seven samples of the actual Lubboc® grafting group. Under the histological examination, a considerable portion of the grafted substitutes has been absorbed and thus a porous structure has been already lost. A new bone has been penetrated in the periphery of the grafted necrotic bone. However, it has been observed that the textile tissues grew up in the periphery of a considerable portion of the necrotic bone, to accordingly prevent a connectivity between the bones. In particular, the central portion of the block has been filled with the textile tissues. It has been reported that these facts would have functioned as disadvantageous factors during a tensile strength test.

In the case of the CSP grafting group, the grafted pellet has been sharply solved from the 2nd week after surgical operation, and then completely absorbed at the 6th week. In this case, a shading of the fusion mass has not been formed. Under the histological examination, a grafted substitute remainder which has existed in small quantity between the horizontal protrusions, has been observed, and the textile tissues have filled the vacancy almost without forming a new bone. Peculiarly, in one sample, an independent new bone island has been observed between the grafted substitute remainders. The observed independent new bone island has been very insignificant. Thus, there has been no meaning of osteoconduction. Finally, it has been judged that it was not possible to use the CSP having no porous structure and having a very high solubility in a living body as an osteoconduction purpose.

In the case of the porous HA grafting group, the structure and volume of the grafted substitute have been well maintained in comparison with the other porous calcium phosphate group under the macrography and microscope examination. Accordingly, a low solubility in a living body has been suggested. A bone growth into the pores was much abundant in the periphery of the block, but the activity was lowered approaching in the central portion. This was a report which could be observed in common in all the porous calcium phosphate grafted substitutes.

In the case of the CPP grafting group, the size of the pore was increased and the thickness of the wall between the pores was thin in comparison with the HA grafting group, which reflected a higher absorption. Meanwhile, the porous structure was well maintained and a new bone was abundantly formed into the porous structure. Also, a new bone showed an appearance of a mature bone whose lamellation was well accomplished. Also, under the manual palpation in these two groups, a fusion ratio was significantly high in comparison with the non-grafting group, CSP, TCP/calcium phosphate composition and TCP grafting groups.

Under a tensile strength test for measuring the maximal binding intensity of a fusion mass, no fusion mass connecting between the horizontal protrusions was not formed in the case of the non-grafting group and the CSP grafting group. As a result, since a connection between two spinal bodies was cut off when edge tissues were cut off for the tensile strength test, the tensile strength was evaluated as zero. In the case of the porous HA and calcium phosphate grafting groups, the tensile strengths are 189±46(N) and 191±56(N), respectively, which were significantly higher in comparison with those of the non-grafting group, Lubboc®, CSP, TCP/CPP and TCP grafting groups. The average tensile strengths of the autograft group and the HA/TCP grafting group were located in the middle of the values of the other groups, but had no significant differences in comparison with the other groups. The tensile strength of the grafted substitute resulted in correlation with the macrography, manual palpation and histological examinations. That is, till the 12th week, the fusion masses of the HA and CPP grafting groups where the pore structure was maintained, were solidly formed. Meanwhile, the fusion masses of the non-grafting group, CSP, TCP/calcium phosphate and TCP grafting groups were loose in their connection. As a result, the fusion masses were separated even in a low tensile load. When this report is reviewed with the results of the manual palpation and the histological examinations, a porous structure should be maintained till the 12th week, which is essential for an osteoconduction or plays a very important role of the osteoconduction. Also, in order to develop a calcium phosphate porous artificial bone, the porous structure should be considered above all the other physical features.

The calcium phosphate grafted substitute is absorbed in a living body, in which case calcium and phosphate are separated. This can increase a concentration in the serum when these separated calcium and phosphate are absorbed, and further induce complications due to a high calcium symptom and a high phosphate symptom in blood. However, as can be seen from the results, the calcium phosphate porous grafting group does not induce a peculiar serum concentration change in comparison with the negative and positive control groups and the other artificial bone grafting groups. Accordingly, the present invention has no problem of induction of the complications due to the separation of the calcium and phosphate in the living body.

In the result of the above-described experiments, a CSP (calcium sulfate pellet) is difficult to be used alone for an osteoconduction due to the porous structure deficiency and the excessive solubility in the living body, in the case of an experimental research where the osteoconduction of the porous calcium phosphate grafting substitutes having a respectively different compositions are observed using a lumbar vertebrae rear-outer fusion model of the New White rabbit, and the observed result is compared with those of the autogeneous bone and the existing artificial bone products. A β-calcium pyrophosphate porous body has an osteoconduction and a mature fusion mass creation capability, similar to the autogeneous bone and the HA porous body, and reveals a more excellent biodegradable capability than that of the HA. Accordingly, the β-calcium pyrophosphate has been judged as the most ideal material among various calcium phosphate compounds when a porous artificial bone is manufactured. Also, since an interruption of the continuous osteoconduction can be observed in the grafted substitutes where a porous structure has been lost during a bone fusion process, it has been judged that the porous structure be essential for a new bone creation through an osteoconduction.

In the case that various types of calcium phosphate compounds are grafted into a living body, the calcium and phosphate change in the serum according to the solution of the calcium and phosphate has no significant differences from those of the autogeneous bone and the non-grafting groups. Thus, an adverse reaction will not be expected.

TABLE 4

|  | Kind of grafted substitutes | Fusion ratio | Average tensile strength (N) |
|---|---|---|---|
| 1st Group | Autogeneous bone | 7/7 | 138 ± 9 |
| 2nd Group | No graft | 0/9 | 0 |
| 3rd Group | Lobboc ® | 6/7 | 102 ± 43 |
| 4th Group | Osteoset ® | 0/10 | 0 |

TABLE 4-continued

| | Kind of grafted substitutes | Fusion ratio | Average tensile strength (N) |
|---|---|---|---|
| 5th Group | HA | 8/10 | 189 ± 46 |
| 6th Group | HA/β-TCP | 6/10 | 128 ± 54 |
| 7th Group | β-TCP | 3/8 | 120 ± 10 |
| 8th Group | β-TCP/calcium pyrophosphate | 5/10 | 140 ± 53 |
| 9th Group | Calcium pyrophosphate | 7/7 | 191 ± 56 |

(Lubboc ®: Bone substitute obtained by re-processing calf bones;
Osteoset ®: Bone substitutes made of gypsum (Calcium Sulfate, $CaSO_4$);
HA: Hydroxyapatite, $Ca_{10}(PO_4)_6(OH)_2$;
TCP: Tricalcium Phosphate, $Ca_3(PO_4)_2$;
Calcium pyrophosphate: $Ca_2P_2O_7$;
Apatite/β-TCP: Composition mixed by weight ratio of 1:1;
β-tricalcium phosphate/calcium pyrophosphate: Composition mixed by weight ratio of 1:1; MgO of 1 weight is added from the 5th group to the 9th group)

As illustrated in Table 4, the porous body having the most excellent bone fusion capability is the porous body manufactured with the calcium pyrophosphate of the first embodiment. The calcium pyrophosphate porous body is much more excellent that the currently commercialized artificial bone product and the autogeneous bone grafting groups. Thus, it can be seen that the bioaffinity of the bioceramic composition according to the present invention is excellent.

As described above, the present invention provides a more ideal artificial bone substitute having a high bone agglutination ratio, a bone fusion intensity, in particular, a relatively high bioabsorptive property in comparison with an existing artificial bone substitute.

As described above, the present invention has been described with respect to particularly preferred embodiments. However, the present invention is not limited to the above embodiments, and it is possible for one who has an ordinary skill in the art to make various modifications and variations, without departing off the spirit of the present invention.

What is claimed is:

1. A first powder selected from the group consisting of magnesium oxide (MgO), magnesium substituted calcium pyrophosphate ($Ca_{2-x}Mg_xP_2O_7$), magnesium pyrophosphate ($Mg_2P_2O_7$), and calcium magnesium pyrophosphate ($CaMgP_2O_7$), and combinations thereof; and a second powder of calcium pyrophosphate ($Ca_2P_2O_7$), said first and second powders being mixed, pressure-formed and then sintered at a temperature range of 1000–1200° C. thereby forming a porous body.

2. The bone graft substitute composition as recited in claim 1, wherein said porous body has a plurality of interconnected pores of 200~600 μm in size and a three-dimensionally connected porous structure.

3. The bone graft substitute composition as recited in claim 1, wherein said magnesium oxide (MgO) is mixed at 0.1–10 wt %.

4. The bone graft substitute composition as recited in claim 1, wherein said magnesium substituted calcium pyrophosphate ($Ca_{2-x}Mg_xP_2O_7$) is mixed at 0.1–75 wt %.

5. The bone graft substitute composition as recited in claim 1, wherein said magnesium pyrophosphate ($Mg_2P_2O_7$) is mixed at 0.2–75 wt %.

6. The bone graft substitute composition as recited in claim 1, wherein said calcium magnesium pyrophosphate ($CaMgP_2O_7$) is mixed at 0.2–75 wt %.

* * * * *